(12) United States Patent
Okada et al.

(10) Patent No.: US 7,608,093 B2
(45) Date of Patent: Oct. 27, 2009

(54) TREATMENT METHOD

(75) Inventors: Yuta Okada, Hachioji (JP); Keita Suzuki, Tachikawa (JP)

(73) Assignee: Olympus Corporation, Tokyo (JP)

(*) Notice: Subject to any disclaimer, the term of this patent is extended or adjusted under 35 U.S.C. 154(b) by 205 days.

(21) Appl. No.: 11/089,735

(22) Filed: Mar. 25, 2005

(65) Prior Publication Data

US 2005/0216041 A1 Sep. 29, 2005

Related U.S. Application Data

(60) Provisional application No. 60/556,835, filed on Mar. 26, 2004.

(51) Int. Cl.
*A61B 17/04* (2006.01)

(52) U.S. Cl. .................................................. 606/232

(58) Field of Classification Search ................ 606/139; 600/104; 227/175.1, 66–67; 128/898
See application file for complete search history.

(56) References Cited

U.S. PATENT DOCUMENTS

| | | | |
|---|---|---|---|
| 5,088,979 A | 2/1992 | Filipi et al. | |
| 5,297,536 A | 3/1994 | Wilk | |
| 6,312,437 B1 | 11/2001 | Kortenbach | |
| 6,736,828 B1 * | 5/2004 | Adams et al. | 606/213 |
| 7,179,267 B2 * | 2/2007 | Nolan et al. | 606/153 |
| 7,273,451 B2 * | 9/2007 | Sekine et al. | 600/104 |
| 2001/0049497 A1 * | 12/2001 | Kalloo et al. | 604/164.01 |
| 2001/0049509 A1 * | 12/2001 | Sekine et al. | 604/264 |
| 2002/0022851 A1 * | 2/2002 | Kalloo et al. | 606/151 |
| 2002/0082621 A1 * | 6/2002 | Schurr et al. | 606/151 |

* cited by examiner

*Primary Examiner*—(Jackie) Tan-Uyen T. Ho
*Assistant Examiner*—Melanie Tyson
(74) *Attorney, Agent, or Firm*—Scully, Scott, Murphy & Presser, P.C.

(57) ABSTRACT

In the treatment method of the present invention, the operation is performed in the following steps: an apparatus is perorally inserted in the stomach, a distal end portion of the apparatus inserted in the stomach is introduced from the stomach into the peritoneal cavity, a membrane of part of the outer wall of the abdominal esophagus is removed by the distal end portion of the apparatus which is introduced in the peritoneal cavity, the distal end portion of the apparatus which is introduced in the peritoneal cavity is returned therefrom into the stomach, the stomach fundus is perorally pulled to the part of the outer wall of the abdominal esophagus, and the pulled stomach fundus is fixed to the part of the outer wall of the abdominal esophagus.

14 Claims, 16 Drawing Sheets

TREATMENT METHOD

CROSS-REFERENCE TO RELATED APPLICATIONS

This application claims the benefit of U.S. Provisional Application No. 60/556,835, filed Mar. 26, 2004.

BACKGROUND OF THE INVENTION

1. Field of the Invention

The present invention relates to a treatment method for gastroesophageal reflux disease.

2. Description of the Related Art

Conventionally, it is well known as gastroesophageal reflux disease (hereinafter referred to as GERD) that acid in the stomach flows back toward the esophagus side. It is thought that the GERD occurs when the reflux preventing function of the cardiac region lowers due to abnormality of a lower esophageal sphincter.

As a treatment method for the GERD, a Nissen surgical operation which is a surgical treatment is well known. In the Nissen surgical operation, the stomach fundus is surgically wound around the esophagus in the pertitoneal cavity, thereby re-forming the cardiac region. The esophagus is squashed and closed when the stomach fundus wound around the esophagus expands. Consequently, the reflux of acid in the stomach is prevented.

Another treatment method for the GERD is disclosed in U.S. Pat. No. 5,088,979. In this treatment method, the esophagus is pushed into the stomach, and is then fixed to the stomach such that the pushed part of the esophagus is kept inside of the stomach. The pushed part of the esophagus is squashed due to expansion of part of the stomach which is close to the gastroesophageal junction, thereby preventing the reflux of acid in the stomach.

A further treatment method for the GERD is disclosed in U.S. Pat. No. 6,312,437. In this treatment method, tissues of the gastroesophageal junction are pulled down into the stomach, and the stomach fundus is pulled and fixed to an outer wall of the pulled tissues of the gastroesophageal junction. The pulled tissues of the gastroesophageal junction are squashed due to expansion of part of the stomach which is close to the gastroesophageal junction, thereby preventing the flux of acid in the stomach.

U.S. Pat. No. 5,297,536 discloses a treatment method in which an incision is formed in the body wall, a surgical instrument is inserted into the peritoneal cavity through the incision, and a surgical treatment is carried out. Furthermore, U.S. patent application No. 2001/0049497 discloses an apparatus having an endoscope and an overtube into which the endoscope is to be inserted. The apparatus is perorally inserted into the stomach, and is then projected into the peritoneal cavity through the gastric wall. Thereafter, the endoscope is inserted into the peritoneal cavity along the overtube, clip forceps, etc. are projected from a distal end portion of the endoscope through an instrument channel thereof, and then placement of clips, etc. are carried out.

BRIEF SUMMARY OF THE INVENTION

A treatment method according to an embodiment of the present invention comprises: perorally inserting an apparatus into a stomach; introducing a distal end portion of the apparatus inserted in the stomach from the stomach into a peritoneal cavity; removing a membrane of part of an outer wall of an abdominal esophagus; returning the distal end portion of the apparatus introduced in the peritoneal cavity into the stomach; perorally pulling a stomach fundus to the part of the outer wall of the abdominal esophagus; and perorally fixing the pulled stomach fundus to the part of the outer wall of the abdominal esophagus.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be explained with reference to FIGS. 1 to 19. In a treatment method according to the embodiment, a reflux preventing valve for preventing occurrence of a reflux from the stomach of a living body to the esophagus is formed to the abdominal esophagus. To be more specific, in this treatment method, an apparatus is perorally introduced from the stomach into the peritoneal cavity, and the peritoneum and fat, etc. of part of an outer wall of the abdominal esophagus are removed through the peritoneal cavity by using the apparatus. Then, the stomach fundus is pulled and fixed to the above part of the outer wall of the abdominal esophagus. The above two steps will be explained in detail.

Figure 1:
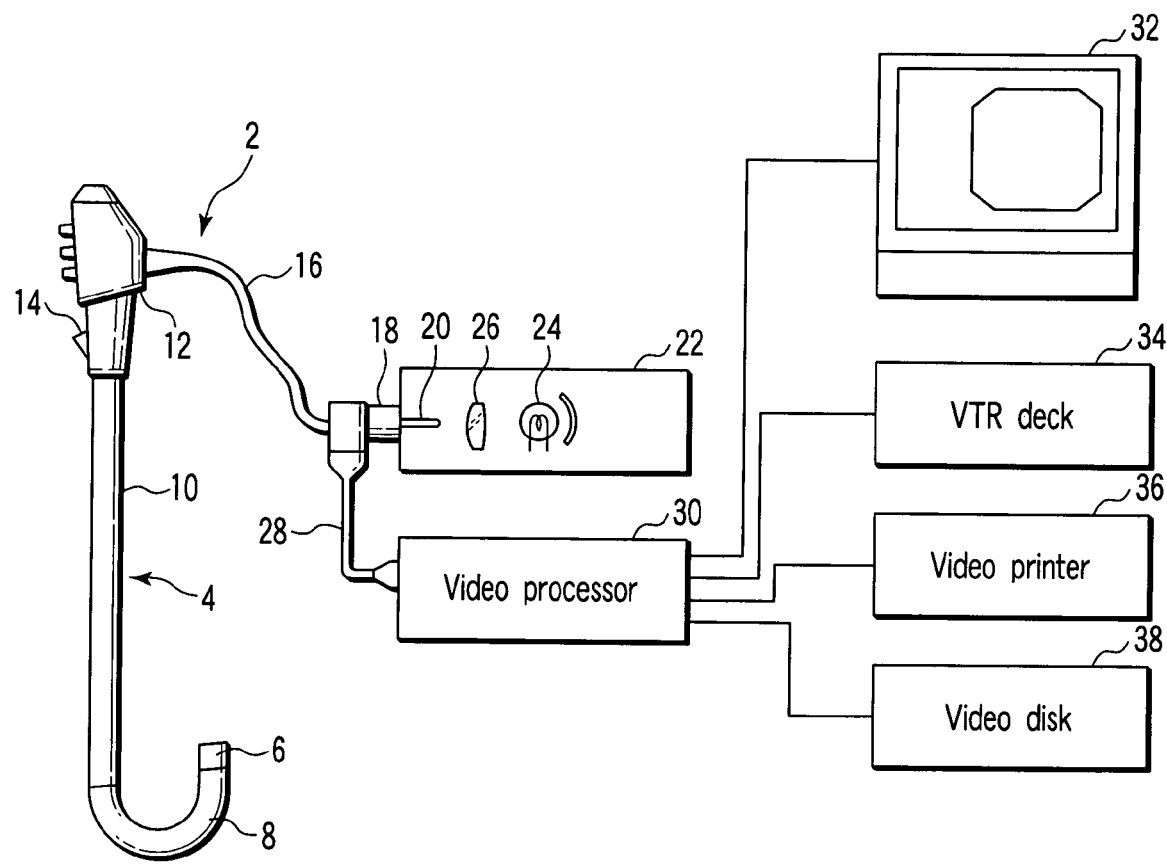
FIG. 1 is an explanatory view showing an endoscope system for use in the treatment method according to an embodiment of the present invention.

First, the step in which the apparatus is perorally introduced from the stomach into the peritoneal cavity, and the peritoneum and fat, etc. of part of an outer wall of the abdominal esophagus are removed through the peritoneal cavity by using the apparatus will be explained with reference to FIGS. 1 to 12. The devices used in the process will be explained with reference to FIGS. 1 to 4. FIG. 1 shows an endoscope 2. The endoscope 2 has substantially the same structure as an endoscope known as an electronic endoscope or a fiber type endoscope.

The endoscope 2 includes an elongated endoscope insertion portion 4 to be inserted into a body cavity. The endoscope insertion portion 4 is formed by connecting an endoscope distal end structural portion 6, an endoscope bending portion 8 and an endoscope flexible tube portion 10 in this order from its distal end. At a proximal end portion of the endoscope insertion portion 4, an endoscope control section 12 is provided. The endoscope control section 12 includes an endoscope operating handle, not shown, for bending operation of the endoscope bending portion 8. The endoscope bending portion 8 can be bent in four directions.

Furthermore, in the endoscope insertion portion 4, an instrument channel 14, into which medical instrument such as forceps are to be inserted, is formed in the longitudinal direction of the endoscope insertion portion 4. A distal end portion of the instrument channel 14 is open at the distal end portion of the endoscope insertion portion 4, and a proximal end portion of the instrument channel 14 is open at the endoscope control section 12.

A universal code 16 is provided to extend from the endoscope control section 12. In the universal code 16, a light guide of an illuminating optical system and a transmission cable of an observing optical system, etc. are inserted. Also, a connector 18 is provided at an extension end portion of the universal code 16. At the connector 18, a light guide connector 20 is provided, and is connected to a light source device 22. The light source device 22 includes a lamp 24 and a condensing lens 26. From the connector 18, a scope cable 28 is extended, and is connected to a video processor 30. The video processor 30 is connected to a monitor 30, a VTR deck 34, a video printer 36 and a video disk 38, etc.

Figures 2, 3:
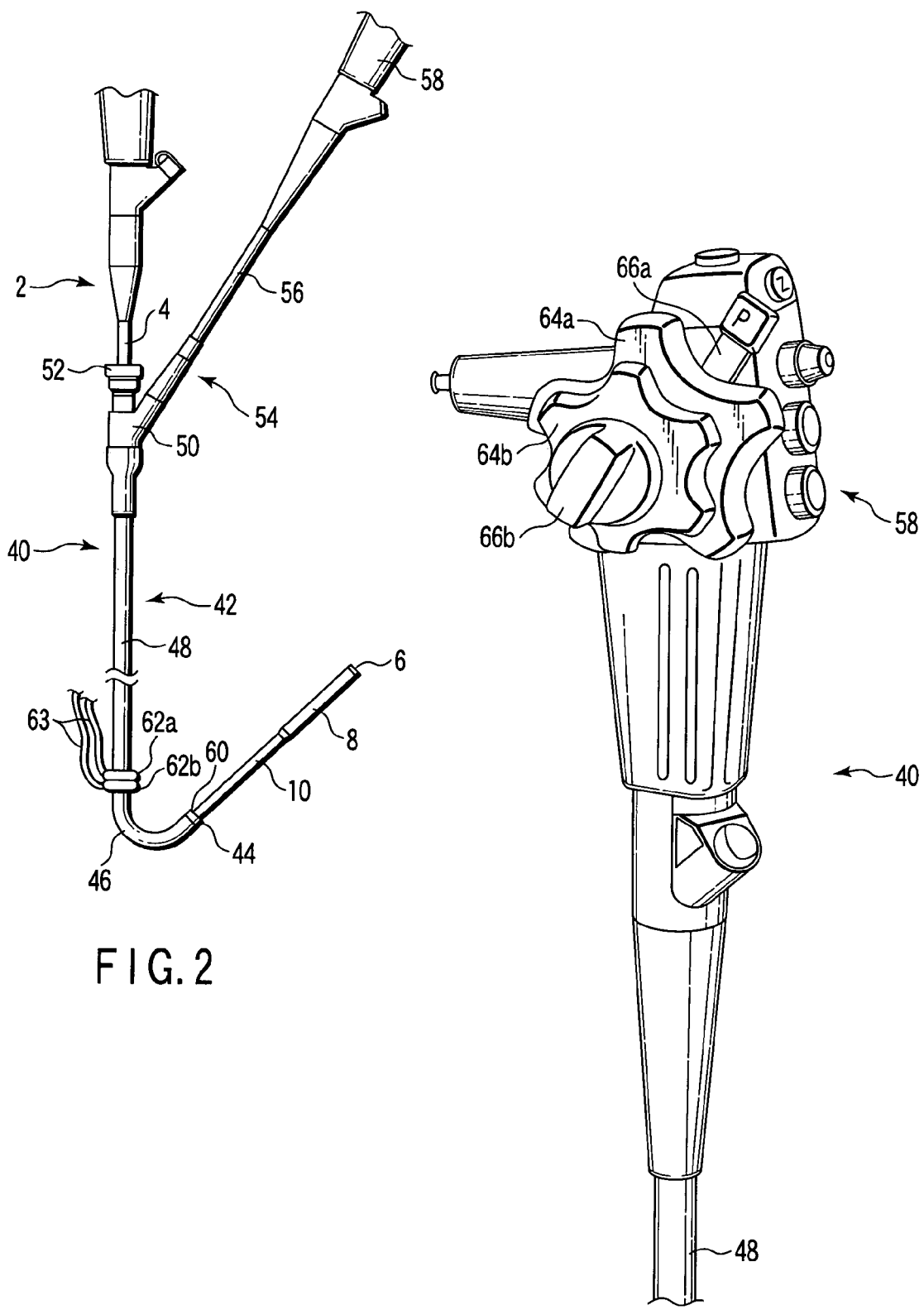
FIG. 2 is a side view showing the endoscope apparatus for use in the treatment method according to the embodiment of the present invention.
FIG. 3 is a perspective view showing a control section of a bending-overtube for use in the treatment method according to the embodiment of the present invention.

An endoscope apparatus including the endoscope 2 and a bending-overtube 40 will be explained with reference to FIG. 2. As shown in FIG. 2, the bending-overtube 40 is provided with an insertion portion 42 which has the same structure as the endoscope 2. To be more specific, the insertion portion 42 is formed by connecting a distal end structural portion 44, a bending portion 46 and a flexible tube portion 48 in this order from its distal end side. At a proximal end portion of the insertion portion 42, a branch portion 50 is provided. The bending-overtube 40 is branched into an insertion opening portion 52 and a branch end portion 54 at the branch portion 50. The insertion opening portion 52 is projected in the direction of the central axis of the insertion portion 42, and the branch end portion 54 is extended inclined backwards with respect to the central axis of the insertion portion 42. To the branch end portion 54, a soft connection flexible tube 56 is connected. To a terminal portion of the connection flexible tube 56, a control section 58 is provided for bending operation of the bending portion 46.

In the bending-overtube 40, an insertion hole 60 is formed to extend through the insertion portion 42, the branch portion 50 and the insertion opening portion 52. A distal end portion of the insertion hole 60 is open at the distal end structural portion 44, and a proximal end portion of the insertion hole 60 is open at the insertion opening portion 52. The bending portion 46 of the bending-overtube 40 can be bent, with the endoscope 2 inserted in the bending portion 46.

In the embodiment, the bending direction of the bending portion 46 will be defined as follows: in a plane including both of the central axis of the insertion portion 42 and a central axis of the branch end portion 54, bending of the bending portion 46 toward the branch end portion 54 is "upward" bending, and bending of the bending portion 46 in a direction opposite to the upward bending is "downward" bending. Also, in a plane vertical to the above plane, bending of the bending portion 46 toward one side direction is "rightward" bending, and bending of the bending direction 46 in a direction opposite to the rightward bending is "leftward" bending.

The outer diameter of the flexible tube portion 48 is set such that the flexible tube portion 48 can be inserted into the esophagus without great resistance. For example, it is set at approximately 20 mm or less. Furthermore, the length of the flexible tube portion 48 is set at an appropriate value to enable a step, which will be described later, to be carried out. For example, the length from the proximal end portion of the bending portion 46 to the terminal portion of the insertion opening portion 52 is approximately 400 to 800 mm. The bend radius of the bending portion 46 is set within a range of approximately 40 to 70 mm. If it is smaller than the range, and then, for example, if a conventional endoscope having an outer diameter of approximately 10 mm is used, the endoscope receives a great resistance when it is inserted into the insertion hole 60 of the bending-overtube 40, as a result of which it is difficult to push the endoscope forwards. In addition, the maximum bend angle of the bending portion 46 in each of upper, lower and right and left directions is set at an appropriate angle more than 180°, with the endoscope 2 inserted in the bending portion of the bending-overtube 40.

The above-mentioned values of the bending-overtube 40 are specified as examples. That is, the dimensions of the bending-overtube 40 are not limited to the values. For example, the above bend radius can be changed in accordance with the outer diameter of the insertion portion 42 and the flexibility of the flexible tube portion 48, etc.

At the outer surface of a boundary portion between the bending portion 46 and the flexible tube portion 48, first and second balloons 62a and 62b, which are annularly formed, are arranged closely in the axial direction of the insertion portion 42. To the first and second balloons 62a and 62b, tubes 63 are connected. The first and second balloons 62a and 62b can be expanded and contracted by injecting and sucking fluid into and from terminal portions of the tubes 63. The first and second balloons 62a and 62b are formed such that they are each formed in a shape of a doughnut around the central axis of the insertion portion 42 when they are expanded.

The structure of the control section 58 will be explained in detail with reference to FIGS. 2 and 3. In the operation portion 58, a UD bending knob 64a and an RL bending knob 64b are provided coaxial with each other. When the UD bending knob is rotated, the bending portion 46 is bent in the upward or downward direction. Similarly, the RL bending knob 64b is rotated, the bending portion 46 is bent in the leftward or rightward direction. At the bending knobs 64a and 64b, engagement levers 66a and 66b are provided, respectively. The engagement levers 66a and 66b are operated to fix the bending knobs 64a and 64b in desired rotation positions, respectively. That is, the bending portion 46 can be fixed at a desired angle. Furthermore, it should be noted that the bending-overtube 40 does not have a connection member like the universal code 16 connecting the control section 58 and another device (see FIG. 1), since it does not have an observing function or the like.

Figures 4, 5:
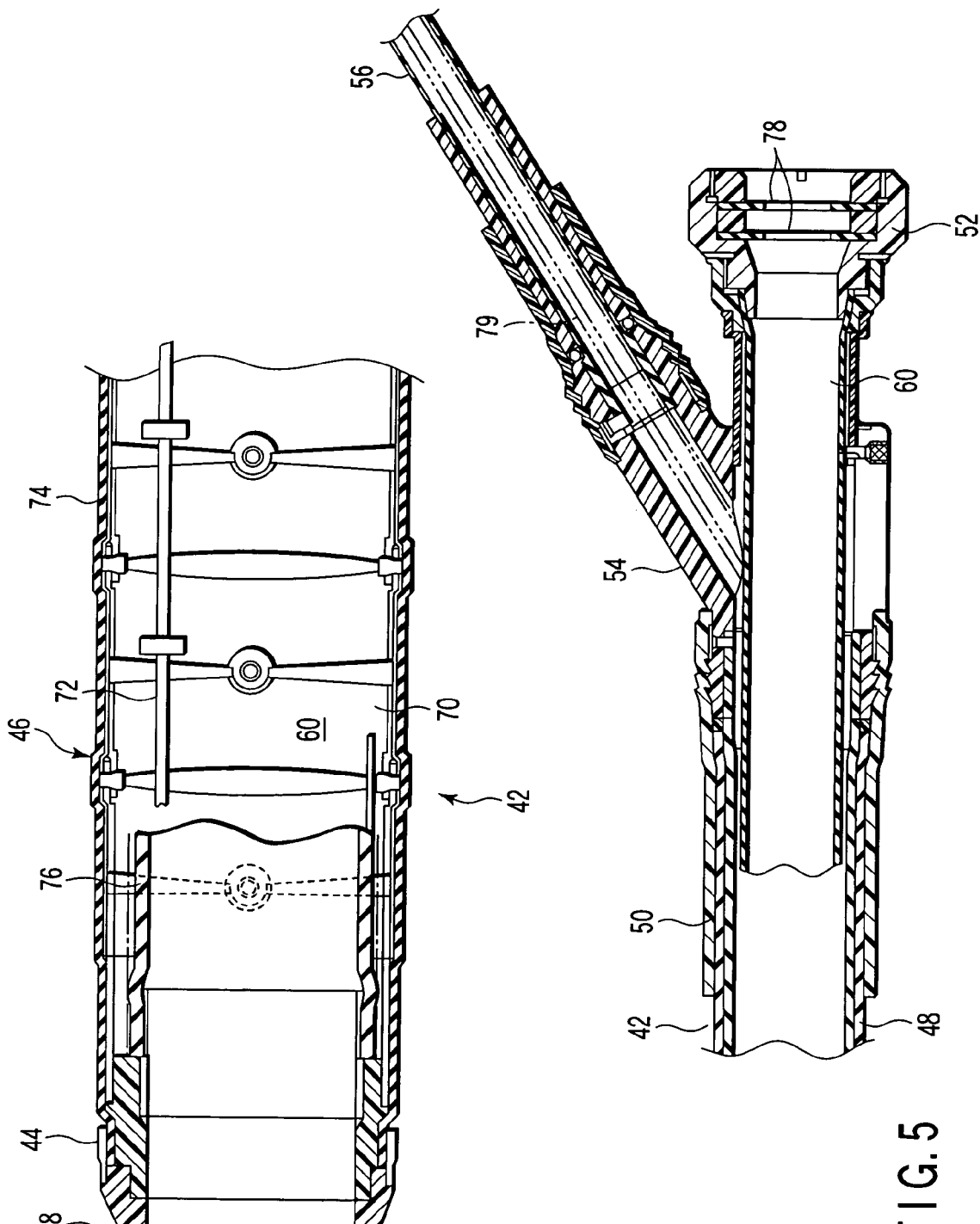
FIG. 4 is a longitudinal sectional view showing a distal end portion of the bending-overtube for use in the treatment method according to the embodiment of the present invention.
FIG. 5 is a longitudinal sectional view showing a branch portion of the bending-overtube and some portions located in the vicinity thereof, for use in the treatment method according to the embodiment of the present invention.
Figure 6:
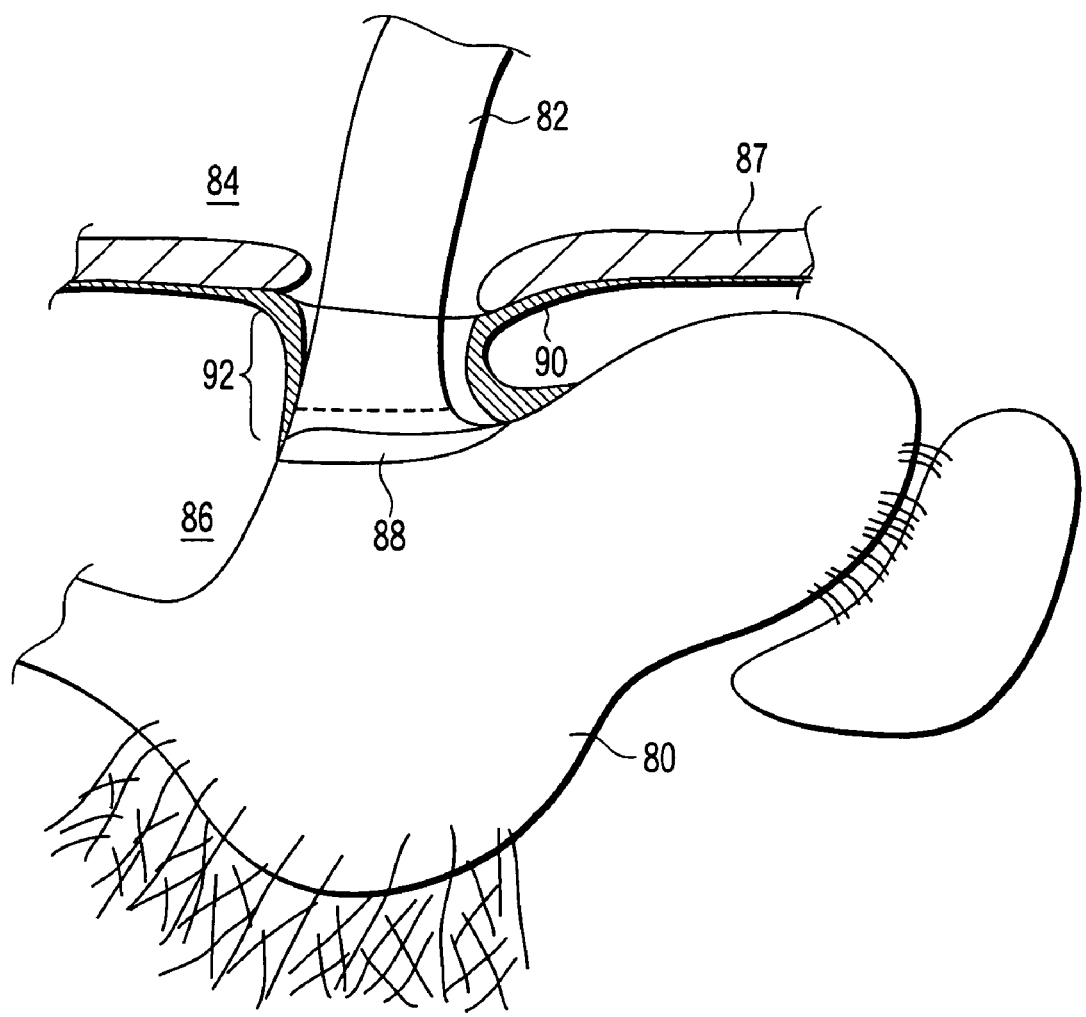
FIG. 6 is an anatomical view showing the esophagus, the stomach and some parts close thereto in a human body.

The structure of the distal end portion of the insertion portion 42 will be explained in detail with reference to FIGS. 2 to 4. The distal end structural portion 44 is substantially cylindrical, and has a taper 68 which extends from its proximal end in such a manner as to be gradually thinner toward the distal end. Furthermore, the bending portion 46 is formed by rotatably connecting substantially cylindrical bending pieces 70 to each other in their axial direction. To the distal end structural portion 44, distal end portions of plurality of pull wires 72 are fixed. The pull wires 72 are connected to the control section 58 through the insertion portion 42, the branch portion 50 and the connection flexible tube 56. When the bending knobs 64a and 64b of the control section 58 are operated, the pull wires 72 are pulled to bend the bending portion 46. Furthermore, the bending portion 46 is covered with an elastic cover 74 formed of elastic material in order to prevent a liquid from entering the bending-overtube 40.

In the bending portion 46, a tube member 76 is inserted. A distal end portion of the tube member 76 is fixed to the distal end structural portion 44. A bore of the distal end structural portion 44 and that of the tube member 76 defines the insertion hole 60 into which the endoscope insertion portion 4 of the endoscope 2 is to be inserted.

The structure of the branch portion 50 will be explained with reference to FIG. 5. As stated above, the insertion portion 42 is connected to the distal end side of the branch portion 50, and the insertion opening portion 52 and the branch end portion 54 are branched from the branch portion 50. Further, the insertion opening portion 52 is projected in the direction of the central axis of the insertion portion 42. The insertion hole 60 linearly extends from the insertion portion 42 to the insertion opening portion 52. In the insertion opening portion 52, a plurality of valves 78 are removably provided. The valves 78 are annular elastic members each of which has an inner diameter slightly smaller than the outer diameter of the endoscope insertion portion 4 (see FIG. 2), which are provided coaxially with the central axis of the insertion hole 60, and which are formed of, e.g., rubber. The endoscope 2 (see FIG. 2) can be inserted into the insertion hole 60 through center holes of the valves 78. When the endoscope 2 (see FIG. 2) is inserted in the insertion hole 60, the valves 78 operate to prevent air, etc. in the insertion hole 60 from flowing therefrom to the outside, and keep the inside of the body cavity leaktight as long as the pressure of the inside of the body cavity is a predetermined value or less.

The branch end portion 54 is extended inclined backwards with respect to the central axis of the insertion portion 42, and the soft connection flexible tube 56 is connected to the branch end portion 54. In the connection flexible tube 56, coil pipes 79 are inserted which extends from the flexible tube portion 48, and in each coil pipe 79, a pull wire (not shown) is inserted which extends from the flexible tube portion 48.

Referring to FIGS. 2 and 3, in the embodiment, the bending-overtube 40, which can be bent in the upward, downward, leftward and rightward directions, is used. However, the structure of the bending-overtube 40 is not limited to the above structure. That is, a bending-overtube 40 which can be bent only in the upward and downward directions, i.e., the two directions, may be used. As the structure of the bending-overtube bendable in the two directions only, it can be considered that the RL bending knob 64b is fixed and unworkable, or the RL bending knob 64b is not provided.

Furthermore, a bending-overtube which can be bent in only one direction from its linear state may be used. As the structure of the bending-overtube bendable in only one direction, it can be considered that the bending-overtube is bent through an angle more than 180° when the UD bending knob 64a is rotated in one direction, and it is returned to its linear state when the UD bending knob 64a is rotated in the opposite direction. Even when the bending-overtube bendable in only one direction is applied, a step, which will be described later, can be carried out as in the case of applying the bending-overtube bendable in the two directions and the bending-overtube bendable in the four directions.

In addition, an indicator for indicating the bending direction of the bending portion 46 may be provided at the branch portion 50 or the control section 58, etc.

Next, the step in which the endoscope is perorally introduced into the peritoneal cavity from the stomach, and peritoneum and fat, etc. of part of the outer wall of the esophagus are stripped off through the peritoneal cavity will be explained with reference to FIGS. 6 to 11. First, the stomach 80, the esophagus 82 and peripheral parts of a human body will be explained with reference to FIG. 6. The esophagus 82 extends from the thorax 84 to the peritoneal cavity 86 through a hiatus of the diaphragm 87, and is connected with the stomach 80 through a gastroesophageal junction 88 in the peritoneal cavity 86. The peritoneum 90 extends from the diaphragm 87 to the gastroesophageal junction 88 to cover the abdominal esophagus 92, and the abdominal esophagus 92 barely exposes to the peritoneal cavity 86.

Figure 7:
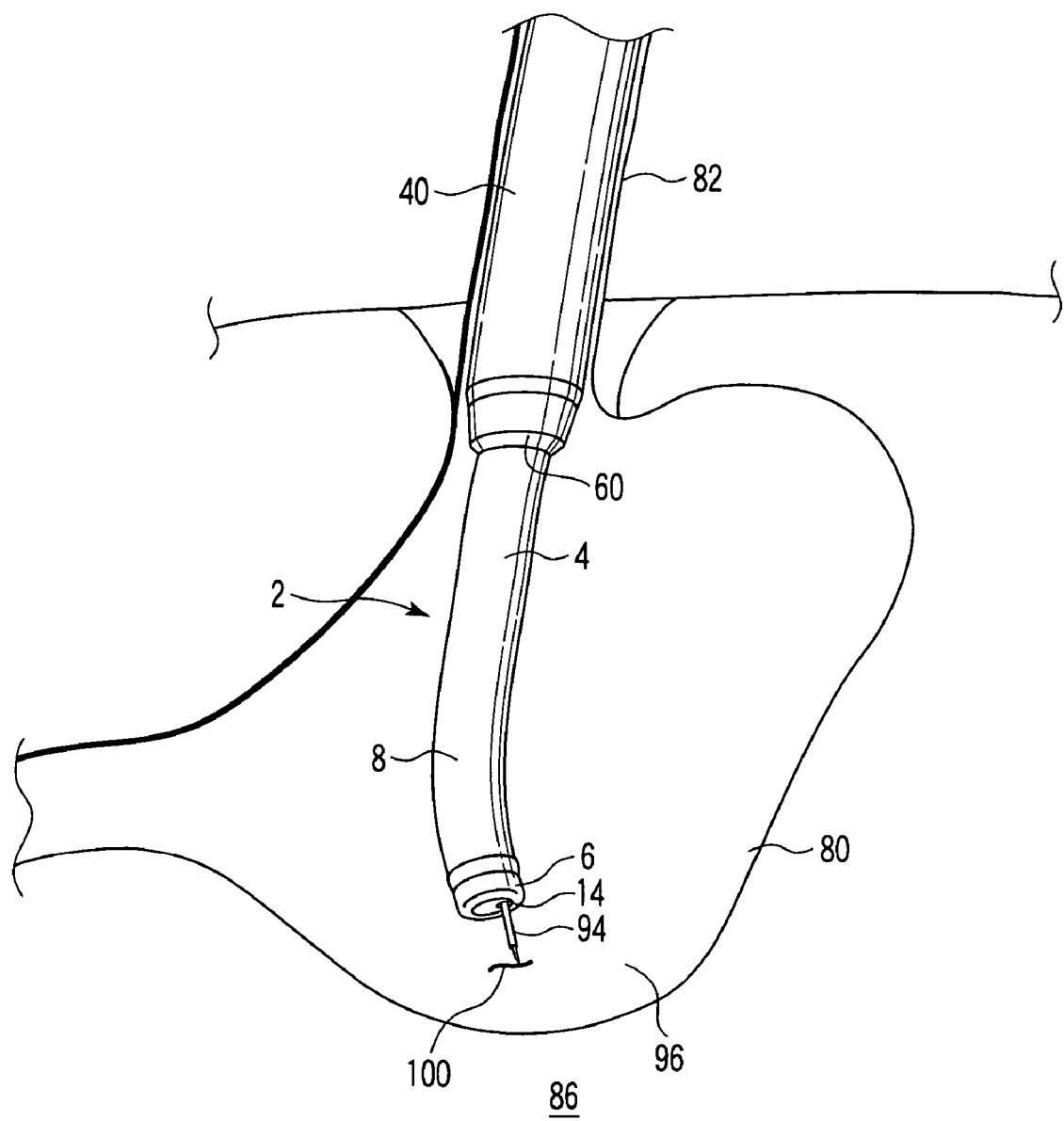
FIG. 7 is a view for use in explaining a step in which part of the stomach is incised, in the treatment method according to the embodiment of the present invention.

The above step will be specifically explained with reference to FIG. 7. The endoscope 2 is inserted into the insertion hole 60 of the bending-overtube 40, and is then projected from the distal end portion of the bending-overtube 40. Then, the endoscope 2 is pushed forwards through the bending-overtube 40, and the distal end portion of the endoscope 2 is inserted into a pharynx portion, the esophagus 82 and the stomach 80 in this order. Thereafter, the bending-overtube 40 is inserted into the pharynx portion, the esophagus 82 and the stomach 80 in this order along the endoscope insertion portion 4.

In this state, e.g., an electrosurgical knife 94 is inserted into the instrument channel 14 of the endoscope 2, and is then projected from the opening of the endoscope structural portion 6. Then, as shown in FIG. 7, an anterior wall 96 of the greater curvature of the stomach is cut by using the electrosurgical knife 94 by a length which is nearly equal to the diameter of the distal end of the endoscope 2. The entire layer, or both mucous membrane and muscle layer of the anterior wall 96, is incised, while pushing the endoscope distal end structural portion 6 against the anterior wall 96. Consequently, an opening portion 100 is formed through which the stomach 80 and the peritoneal cavity 86 communicate with each other.

Figure 8:
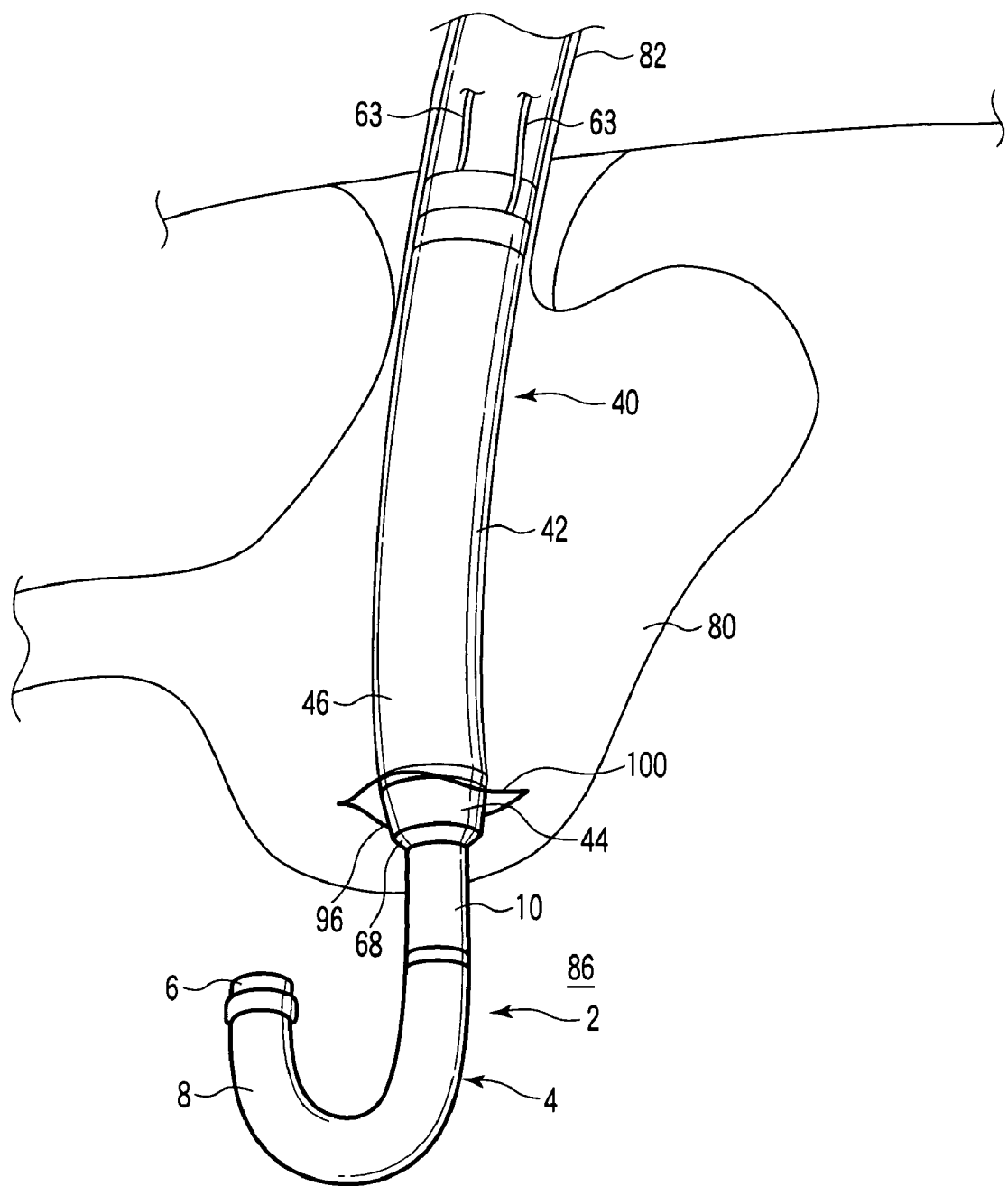
FIG. 8 is a view for use in explaining a step in which an endoscope is moved into the peritoneal cavity, in the treatment method according to the embodiment of the present invention.

Thereafter, the endoscope 2 is pushed toward the opening portion 100, and its distal end portion is introduced from the stomach 80 into the peritoneal cavity through the opening portion 100. Furthermore, the endoscope 2 is pushed forwards, and the endoscope bending portion 8 is located in the peritoneal cavity 86. Then, as shown in FIG. 8, the endoscope bending portion 8 is reversed in such a way as to be bent through an appropriate angle more than 180° and the posture of the endoscope 2 is adjusted so that the opening portion 100 is located within the field of view of the endoscope 2, While checking the state of the opening portion 100 by using the endoscope 2, the bending-overtube 40 is pushed forwards along the endoscope 2, and the distal end portion of the bending-overtube 40 is introduced from the stomach 80 into the peritoneal cavity 86 through the opening portion 100. The distal end portion of the bending-overtube 40 is introduced from the stomach 80 into the peritoneal cavity 86, while pushing and opening the opening portion 100 by means of the taper 68. Furthermore, under observation using the endoscope 2, the bending-overtube 40 is pushed forwards along the endoscope 2, and the bending portion 46 is introduced into the peritoneal cavity 86 by a distance nearly half the entire length of the bending portion 46.

Figure 9:
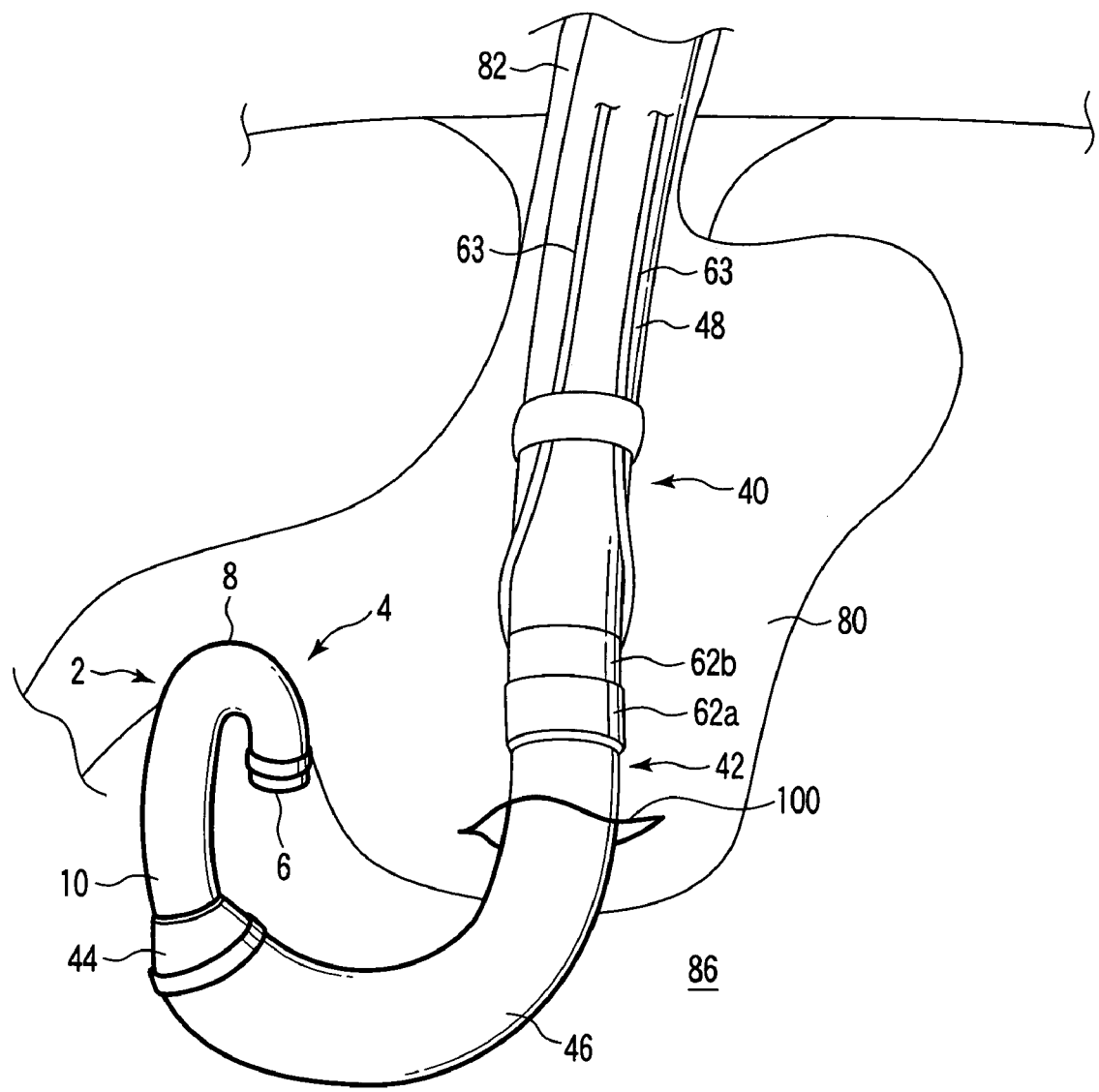
FIG. 9 is a view for use in explaining a step in which the bending-overtube is moved into the peritoneal cavity, in the treatment method according to the embodiment of the present invention.

Thereafter, as shown in FIG. 9, the bending portion 46 is bent through approximately 90° in the upward direction. The posture of the bending-overtube 40 is adjusted such that the bending portion 46 is bent in a plane parallel to the anterior and posterior walls of the stomach 8. Under observation using the endoscope 2, the posture of the endoscope 2 can be grasped based on the arrangement of internal organs in the peritoneal cavity 86. Also, it should be noted that in the case where the indicator indicating the bending direction of the bending portion 46 is provided at the control section 58 or the branch portion 50, etc., the bending direction of the bending portion 46 can be grasped based on the positional relationship between the position of a patient and the indicator or the like.

Under observation with the endoscope 2, the bending-overtube 40 is further pushed into the peritoneal cavity 86, and only the first balloon 62a which is located closer to the distal end side than the second balloon 62b is introduced into the peritoneal cavity 86. Then, fluid is injected into the first and second balloons 62a and 62b from the terminal portion of the tube 63 which is located outside the body of the patient, thereby expanding the first and second balloons 62a and 62b. As a result, as shown in FIG. 10, the anterior wall 96 is held by the first and second balloons 62a and 62b, thus fixing the insertion portion 42 to the anterior wall 96.

Moreover, the bending portion 46 is bent until its bend angle reaches approximately 180°, while grasping the positional relationship between the endoscope apparatus and the internal organs using the endoscope 2. The bend radius of the bending portion 46 falls within a range of approximately 40 to 70 mm, and is relatively small with respect to the inner space of the peritoneal cavity 86. Thus, even when the bending-overtube 40 introduced in the peritoneal cavity 86 is bent, there is a slight possibility that the bending-overtube 40 may contact an internal organ, abdominal wall or the like, and receive a resistance. Thus, the bending-overtube 40 can be reliably bent.

Figure 10:
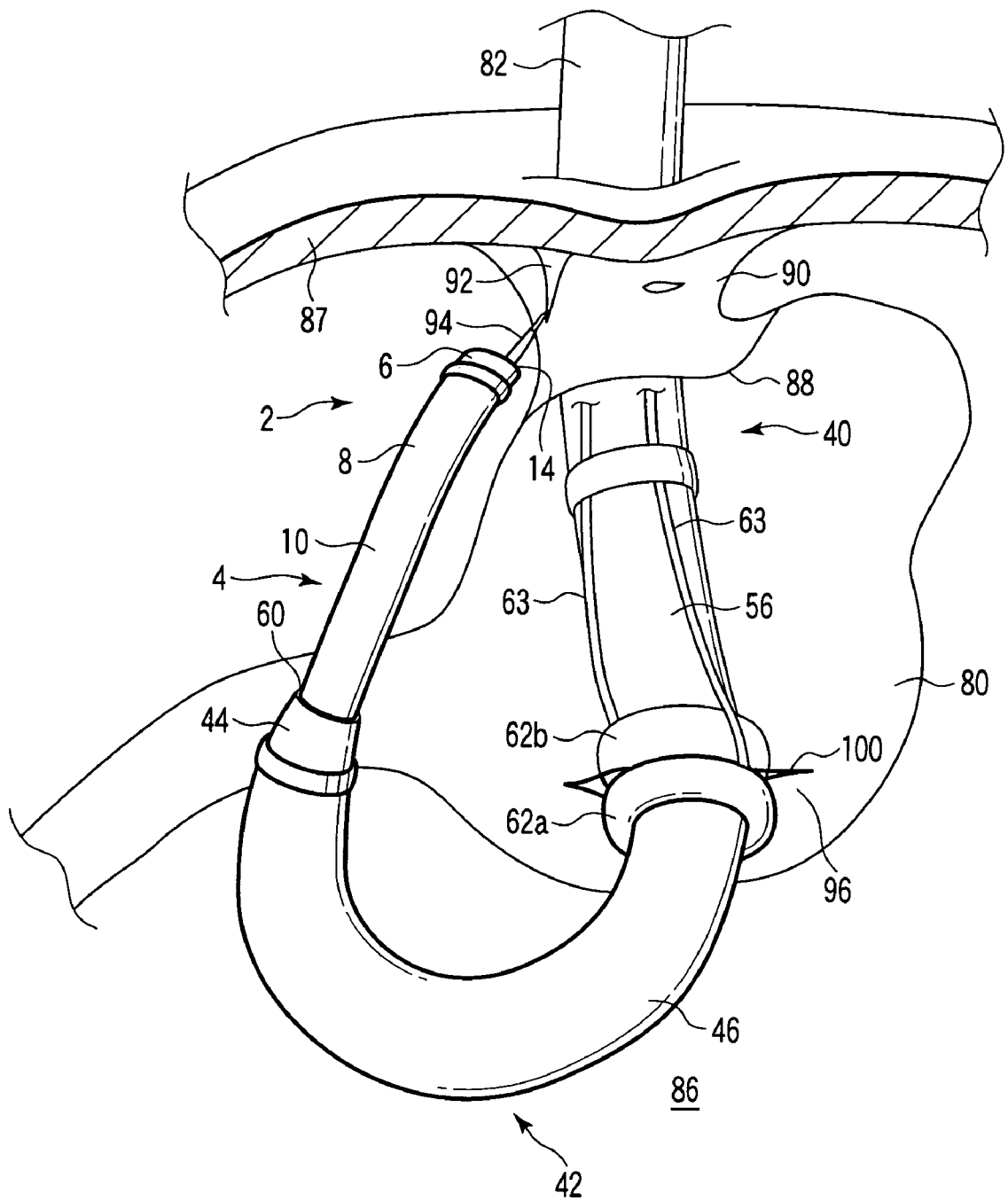
FIG. 10 is a view for use in explaining a step in which the endoscope is brought close to an outer wall of the peritoneal cavity, and a membrane of part of the outer wall of the peritoneal cavity is stripped off, in the treatment method according to the embodiment of the present invention.

Thereafter, as shown in FIG. 10, the endoscope bending portion 8 is returned to the linear state. Then, with an operator's operation on the proximal end side of the apparatus, the endoscope 2 is pushed forwards in the insertion hole 60 of the bent bending-overtube 40, and the distal end portion of the endoscope 2 is pushed forwards in the peritoneal cavity 86. The posture of the bending-overtube 40 is adjusted as occasion demands, so that the distal end portion of the endoscope 2 is moved to reach the vicinity of the abdominal esophagus 92. Then, the electrosurgical knife 94 is projected from the instrument channel 14 of the endoscope 2, and the peritoneum 90 covering the abdominal esophagus 92 from the diaphragm 87 to gastroesophageal junction 88 is incised from the peritoneal cavity side, and is ablated. In such a manner, the abdominal esophagus 92 is sufficiently exposed to the peritoneal cavity 86.

Then, the endoscope 2 and the bending-overtube 40 are pulled back into the stomach 80 in the following manner. The endoscope bending portion 8 is bent to be reversed, and the distal end portion of the bending-overtube 40 is located in the field of view of the endoscope 2 and checked. Then, the endoscope 2 is pulled into the bending-overtube 40 as much as possible. In the case where the bending portion 46 is greatly projected in the peritoneal cavity 86, when it is returned to the linear state, it is easily brought into contact with another internal organ. This is because when the bending portion 46 is bent with respect to its proximal end portion in the peritoneal cavity 86, its bend radius is great. Accordingly, in the embodiment, the following operation is repeated: the bending portion 46 is slightly returned from its bent state toward the linear state, and the bending-overtube 40 is pulled from the peritoneal cavity 86 into the stomach 80 by several centimeters. In such a manner, since the bent state of the bending portion 46 is returned to the linear state by degrees, the bending portion 46 is not easily brought into contact with another internal organic. In the above manner, the bending portion 46 of the bending-overtube 40 is returned to the linear state.

On the other hand, the endoscope 2 is kept bent even after the bending portion is made in substantially the linear state. The bending-overtube 40 is completely pulled into the stomach 80, while checking the distal end structural portion 44 of the bending-overtube 40 in the field of view of the endoscope 2. The endoscope bending portion 8 is returned to the linear state after confirming that bending-overtube 40 is completely pulled from the peritoneal cavity 86 into the stomach 80. Then, the endoscope 2 is pulled from the peritoneal cavity 86 into the stomach 80, and the opening portion 100 is checked within the field of view of the endoscope 2 in the stomach 80.

Figure 11:
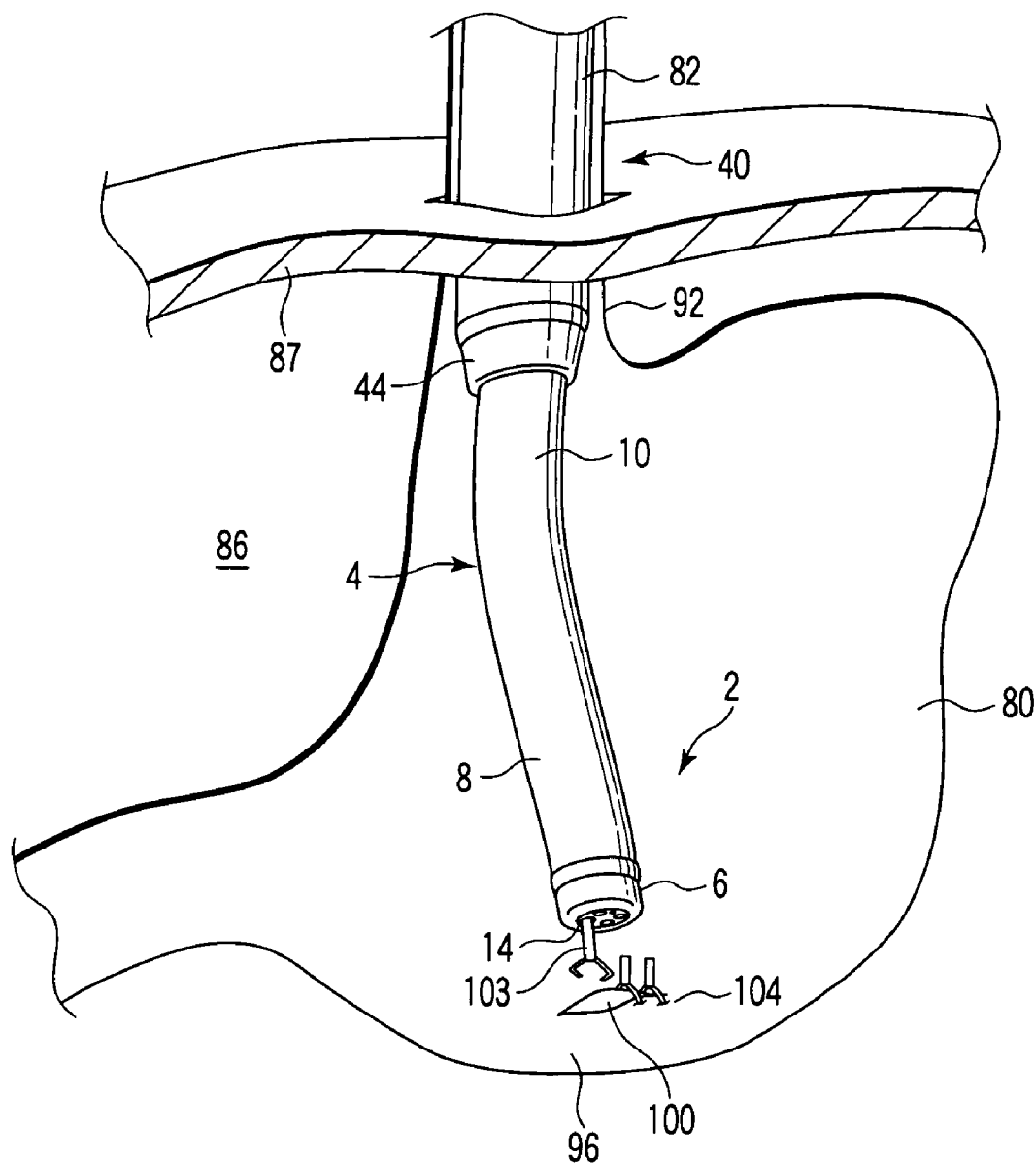
FIG. 11 is a view for use in explaining a step in which the endoscope is returned from the peritoneal cavity into the stomach, and an opening portion formed in the stomach is closed, in the treatment method according to the embodiment of the present invention.

Thereafter, as shown in FIG. 11, clip forceps 103 are projected from the instrument channel 14 of the endoscope 2, and a plurality of clips 104 are located to close the opening portion 100 formed in the anterior wall 96. After the opening portion 100 is completely closed, the endoscope 2 and the bending-overtube 40 are pulled out from the human body.

In the above step, the peritoneum 90 covering the abdominal esophagus 92 is incised and ablated through the peritoneal cavity, as a result of which the abdominal esophagus 92 is sufficiently exposed to the peritoneal cavity 86.

In the step, since the insertion hole 60 of the bending-overtube 60, into which the endoscope 2 is inserted, is linearly shaped, except for the case where the bending portion 46 is bent, the endoscope 2 inserted in the insertion hole 60 of the bending-overtube 60 is also linearly shaped, and can be easily moved forwards/backwards. Furthermore, the endoscope 2 can be easily turned around its central axis within the bending-overtube 40, since the insertion hole 60 of the bending-overtube 40 and the insertion portion 42 of the endoscope 2 are substantially coaxial with each other. In addition, the control section 58 of the bending-overtube 40 can be feely moved so as not to interfere with operations, since it is provided at the terminal portion of the soft connection flexible tube 56 connected to the branch portion 50, thus improving the operability.

A modification of the above structural elements and steps will be explained with reference to FIG. 12. In the modification, the endoscope 2 includes first and second forceps channels 14a and 14b. The endoscope 2 is a multi-bending endoscope, and includes first and second endoscope bending portions 8a and 8b which are arranged adjacent to each other in the axial direction of the endoscope insertion portion 4. The first endoscope bending portion 8a on the distal end side of the endoscope 2 can be bent in four directions. The second endoscope bending portion 8b can be bent in two directions independent of the first endoscope bending portion 8a. At the endoscope control section, operating knobs not shown are provided the number of which varies in accordance with the number of the endoscope bending portions and that of the bending directions thereof.

Figure 12:
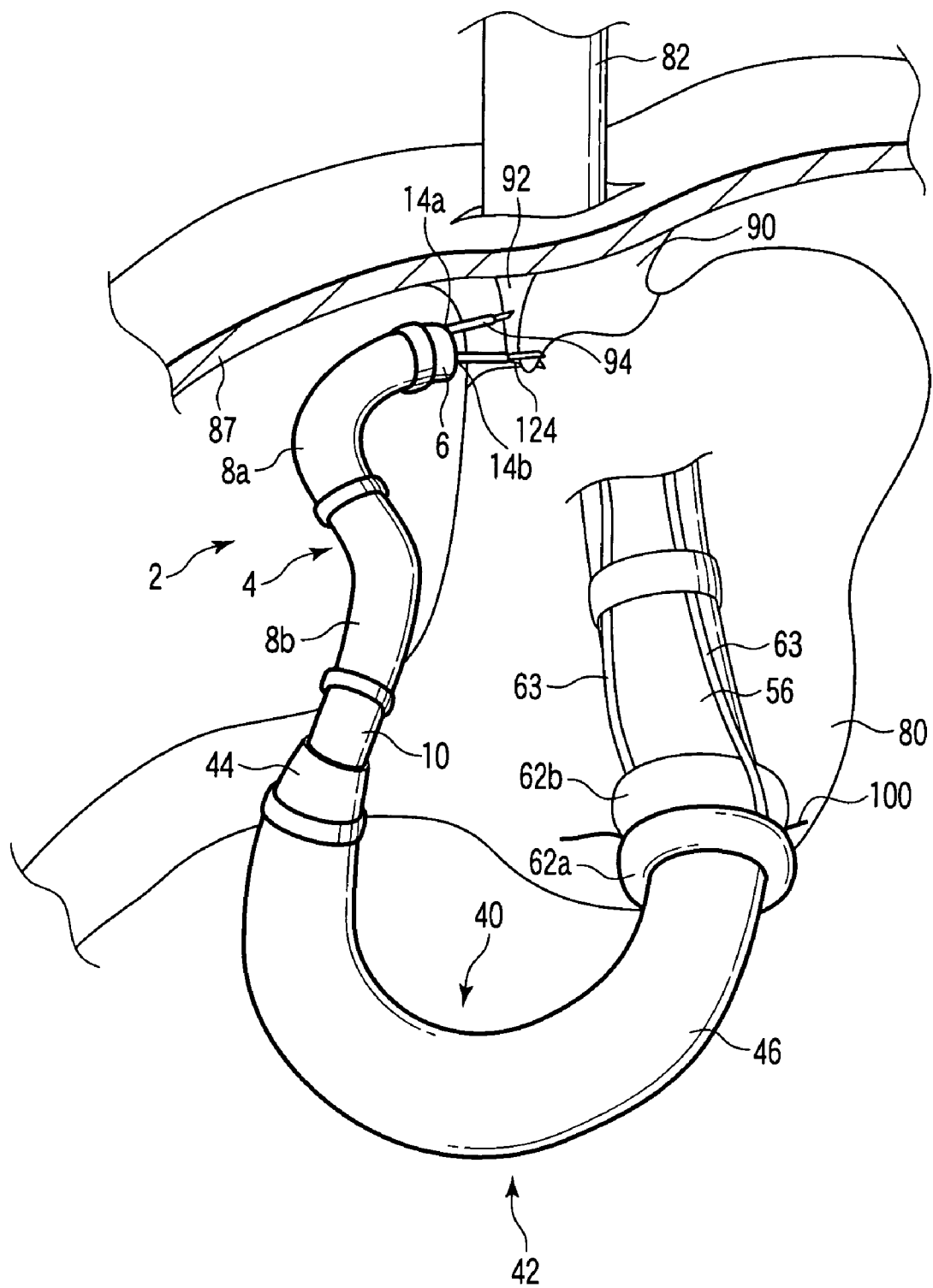
FIG. 12 is a view for use in explaining a step in which the endoscope is brought close to an outer wall of the abdominal esophagus, and a membrane of part of the outer wall is stripped off, in the treatment method according to a modification of the embodiment of the present invention.

As shown in FIG. 12, in the case of ablating the peritoneum 90, the first and second endoscope bending portions 8a and 8b are bent in opposite directions, and the posture of the endoscope insertion portion 4 is adjusted such that the endoscope distal end structural portion 6 is raised, whereby the endoscope distal end structural portion 6 is located in the front of the abdominal esophagus 92. In this state, grasping forceps 124 are projected from the second forceps channel 14b, and part of the peritoneum 90 which is to be incised is grasped and pulled by the grasping forceps 124. Then, the electrosurgical knife 94 is projected from the first forceps channel 14a to incise and ablate the pulled part of the peritoneum 90. It should be noted that the grasping forceps 124 and the electrosurgical knife 94 can be vertically pushed against the peritoneum 90, since the endoscope distal end structural portion 6 is located in the front of the abdominal esophagus 92. Accordingly, the operability is improved.

In the operation for incising and ablating the peritoneum 90, in the above embodiment, the electrosurgical knife 94 is used, and in the above modification of the embodiment, the grasping forceps 124 and the electrosurgical knife 94 are used in combination with each other. However, the above incising and ablating operation can also be carried out by another method.

Figure 13A:
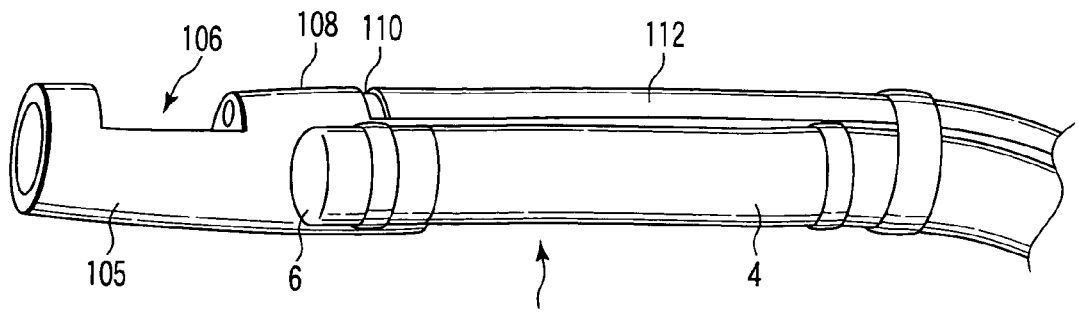
FIG. 13A is a perspective view showing a distal end portion of the endoscope for use in treatment method according to the embodiment of the present invention.

Next, the step in which the stomach fundus is perorally pulled and fixed to the part of the outer wall of the gastroesophageal junction, from which the peritoneum, etc. are stripped off, will be explained. Also, the structural elements used in the step will be explained with reference to FIGS. 13A to 15B. As shown in FIG. 13A, the distal end portion of the endoscope 2 is fitted in a distal end hood 105 as a tube member and an abut member. In the distal end hood 105, a side hole 106 is formed as a communication portion. In the embodiment, the side hole 106 is located in an upper position of the field of view of the endoscope 2; however, it may be located in another position.

Figure 13B:
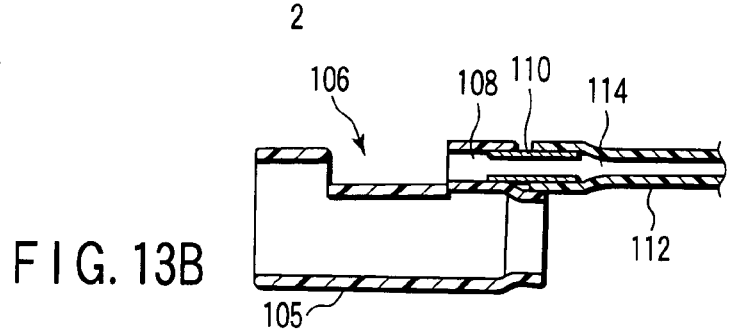
FIG. 13B is a longitudinal sectional view of a distal end hood for use in the treatment method according to the embodiment of the present invention.

As shown in FIG. 13B, on a rear end side of the distal end hood 105, a distal end tube passage 108 is formed to extend in the axial direction of the distal end hood 105. A distal end opening portion of the distal end tube passage 108 is located in substantially the same position as the side hole 106 in a circumferential direction of the distal end hood 105. At a rear end opening portion of the distal end tube passage 108, a connecting pipe 110 is provided to be projected. To the connecting pipe 110, a distal end portion of a distal end hood sheath 112 is connected. The distal end hood sheath 112 extends to the vicinity of the endoscope control section 12 (see FIG. 15A). The distal end tube passage 108, the connecting pipe 110 and the distal end hood sheath 112 define a distal end hood channel 114. The distal end hood channel 114 permits any of kinds of medical instruments to be inserted thereinto from its proximal end portion, and also enables air and water to be sent and sucked through the distal end hood channel 114.

Figure 13C:
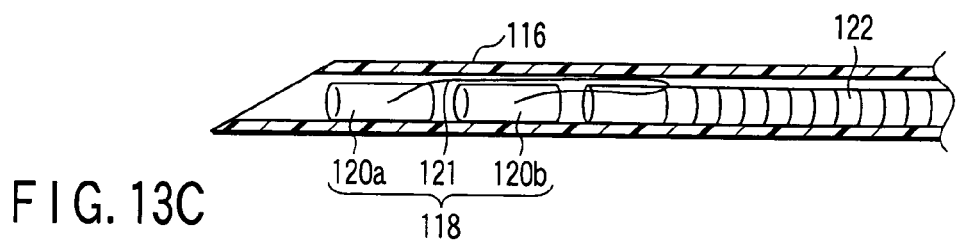
FIG. 13C is a longitudinal sectional view of a puncture needle for use in the treatment method according to the embodiment of the present invention.

A puncture needle 116 to be inserted into the distal end hood channel 114 is shown in FIG. 13C. The puncture needle 116 is formed as a hollow needle, and contains a placement member 118 at its distal end portion. The placement member 118 is formed by connecting first and second T-bars 120a and 120b with a thread 121. The first and second T-bars 120a and 120b are fitted in the puncture needle 116, and the second T-bar 120b is located in the rear of the first T-bar 120a. Also, the puncture needle 116 contains a pusher 122 which is located in the rear of the placement member 118. When the pusher 122 is moved forwards and backwards, the first and second T-bars 120a and 120b can be separately ejected from the distal end portion of the puncture needle 116.

Figure 14A:
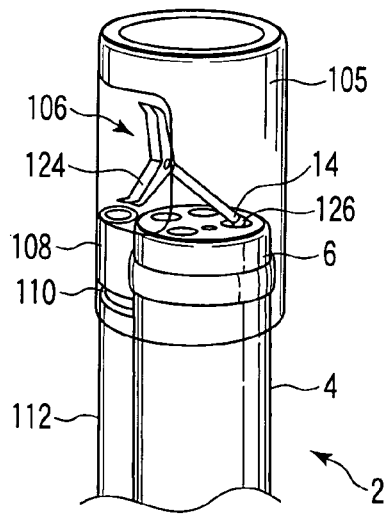
FIG. 14A is a perspective view of the distal end portion of the endoscope for use in the treatment method according to the embodiment of the present invention.

As shown in FIG. 14A, the grasping forceps 124 can be inserted into the instrument channel 14 of the endoscope 2. At the distal end opening portion of the instrument channel 14, an elevator 126 is provided which can adjust the projecting direction of the grasping forceps 124. Due to adjusting of the projecting direction of the grasping forceps 124 with the elevator 126, the grasping forceps 124 can be projected to the outside of the distal end hood 105 through the side hole 106.

Figure 14B:
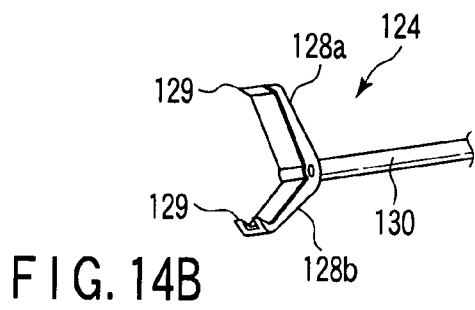
FIGS. 14B and 14C are views showing grasping forceps for use in the treatment method according to the embodiment of the present invention.
Figure 14C:
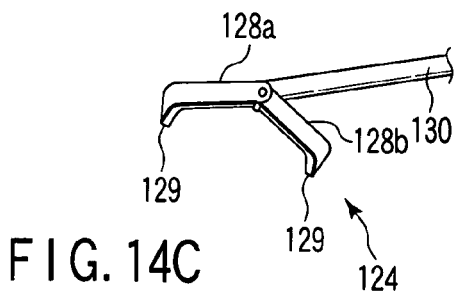

As shown in FIG. 14B, the grasping forceps 124 include first and second grasping portions 128a and 128b which are openable/closable by an operation on the distal end side of the endoscope 2. A sheath 130 extends from a journal portion of the first and second grasping portions 128a and 128b. The first and second grasping portions 128a and 128b can be opened such that they can grasp tissues of the stomach fundus and tissues of the abdominal esophagus which are stacked together. Furthermore, sharp edges 129 for puncturing tissues of a living body are provided at the inner surfaces of the distal end portions of the first and second grasping portions 128a and 128b. Then, as shown in FIG. 14C, a center line between the first and second grasping portions 128a and 128b can be inclined with respect to the sheath 130, and the first and second grasping portions 128a and 128b can be opened asymmetrical with respect to the sheath 130.

Figure 15A:
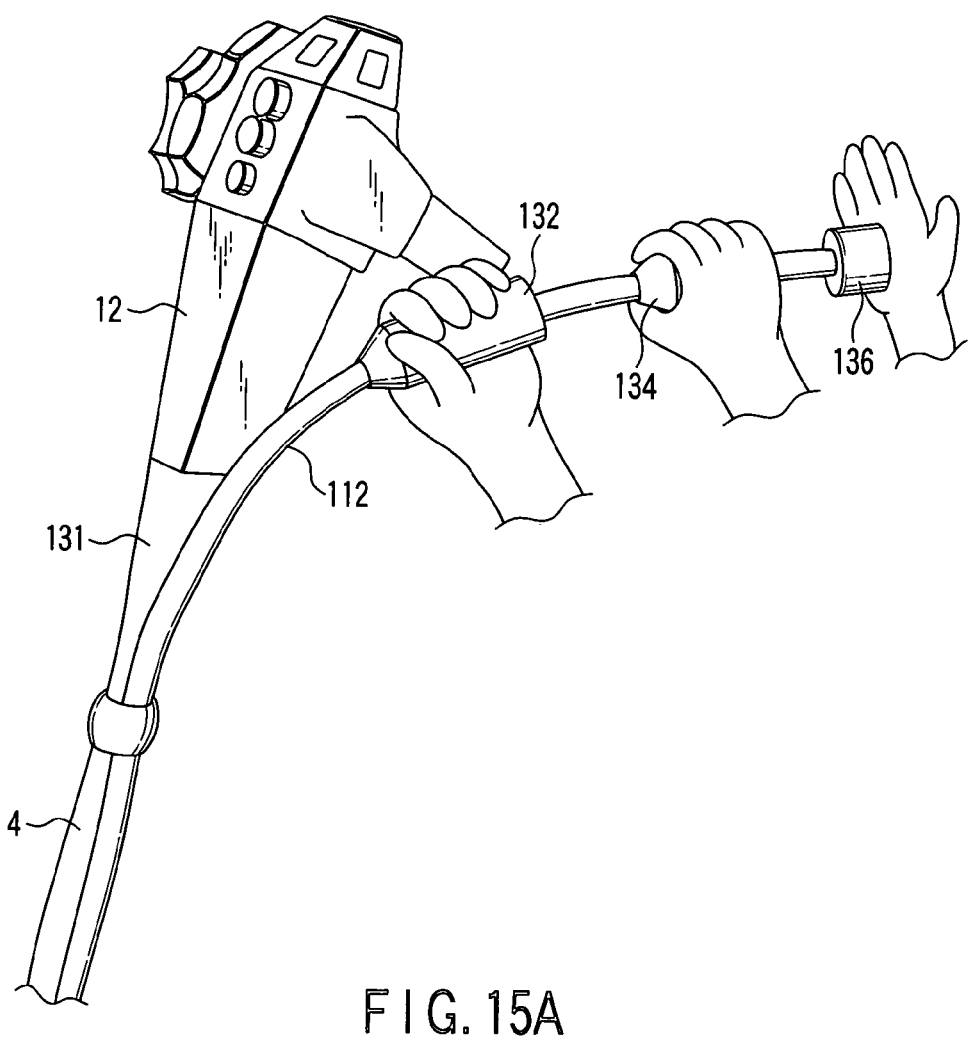
FIG. 15A is a perspective view showing an endoscope control section of the endoscope and a proximal end portion of a distal end hood channel of the endoscope, for use in the treatment method according to the embodiment of the present invention.
Figure 15B:
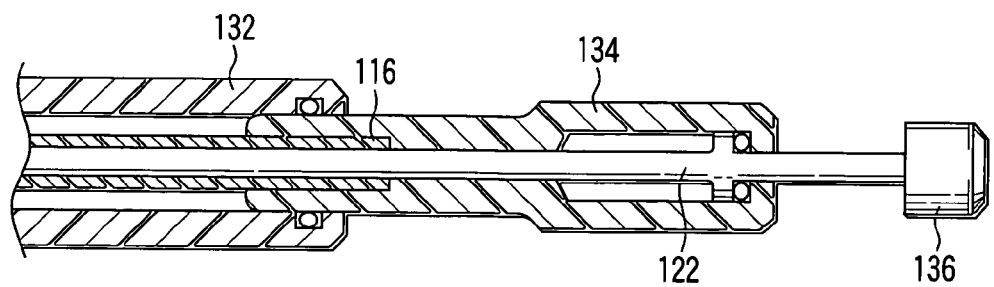
FIG. 15B is a longitudinal sectional view of the distal end hood channel of the endoscope for use in the treatment method according to the embodiment of the present invention.

As shown in FIGS. 15A and 15B, the distal end sheath hood 112 is fixed with a tape or the like to a protection boot 131, which connecting the endoscope control section 12 and the endoscope insertion portion 4 and preventing folding of the endoscope insertion portion 4, and other parts of the insertion portion 4. At the proximal end portion of the distal end hood sheath 112, a sheath handle 132 is provided which is to be gripped by an operator. At a proximal end portion of the sheath handle 132, a needle handle 134 is provided for moving the puncture needle forwards/backwards. At a distal end portion of the needle handle 134, a pusher handle 136 is provided for moving the pusher 122 forwards/backwards.

As shown in FIG. 15B, the sheath handle 132 is substantially cylindrical, and the puncture needle 116 is inserted in an inner hole of the sheath handle 132. Also, the needle handle 134 is substantially cylindrical, and its distal end is fitted from the proximal end side of the sheath handle 132 in the inner hole thereof such that it is movable forwards/backwards. A proximal end portion of the puncture needle 116 is connected to a distal end portion of the needle handle 134. A proximal end side of the needle handle 134 has a diameter larger than that of the distal end side, and is provided as part to be gripped by the operator. A distal end side of the pusher handle 136 is fitted from the proximal end side of the needle handle 134 in an inner hole thereof such that it is movable forwards/backwards. The pusher 122 is inserted in the inner holes of the puncture needle 116 and needle handle 134, and its proximal end portion is connected to the distal end portion of the pusher handle 136. The distal end portion of the pusher handle 136 is provided as part to be pushed by the operator.

Figure 16:
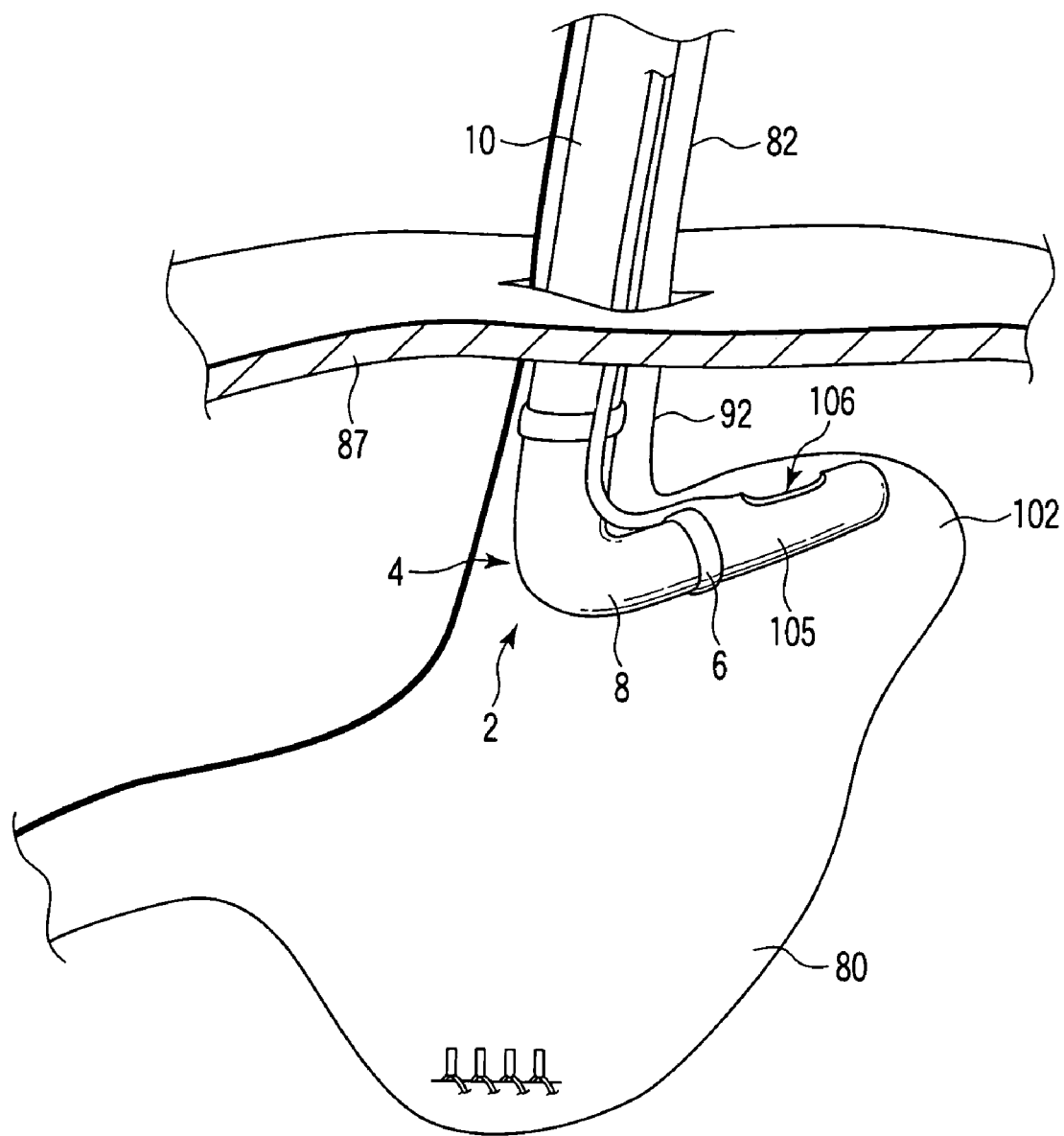
FIG. 16 is a view for use in explaining a step in which the stomach fundus is pulled to part of the outer wall of the abdominal esophagus, the membrane of which is stripped off.

Next, the step in which the stomach fundus is perorally pulled and fixed to the part of the outer wall of the abdominal esophagus 92, from which the peritoneum, etc. are stripped off, will be explained with reference to FIGS. 16 to 18. The endoscope 2 on which the distal end hood 15 is set is inserted perorally from the esophagus 82 into the stomach 82. The posture of the endoscope 2 is adjusted such that the side hole 106 of the distal end hood 105 faces the greater curvature. Then, as shown FIG. 16, the endoscope bending portion 8 is bent such that the distal end portion of the distal end hood 105 is moved from a position under a lower end of the esophagus 82 toward the stomach fundus 102, and the distal end portion of the distal end hood 105 is abutted against an inner surface of the stomach fundus 102. The side hole 106 of the distal end hood 105 faces the stomach fundus 102 and toward the abdominal esophagus. In the embodiment, the side hole 106 is located in the upper position of the field of view of the endoscope 2, and the endoscope bending portion 8 of the endoscope 2 is bent upwards in above step.

Figure 17A:
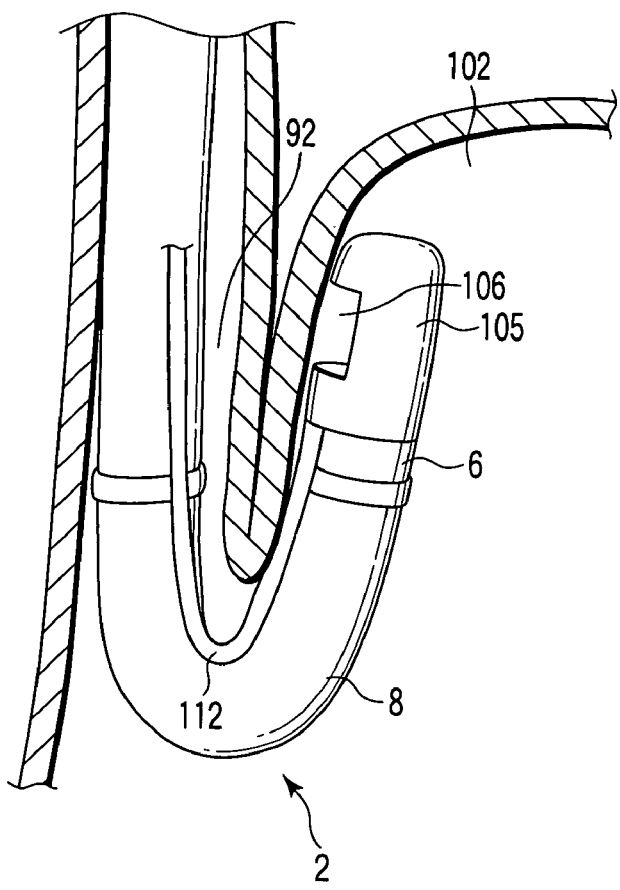
FIG. 17A is a view for use in explaining a step in which the stomach fundus is brought into contact with the above part of the outer wall of the abdominal esophagus, in the treatment method according to the embodiment of the present invention.
Figure 17B:
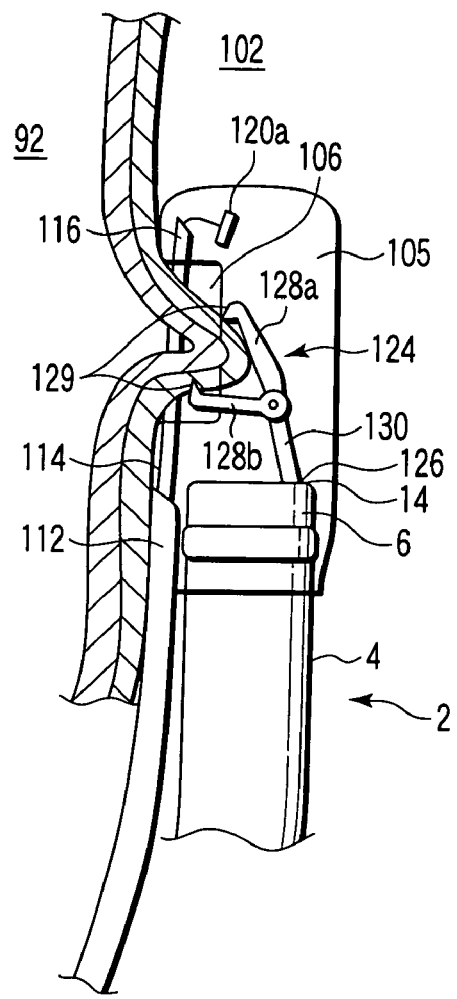
FIG. 17B is a view for use in explaining a step in which the stomach fundus is fixed to the part of the outer wall of the abdominal esophagus, in the treatment method according to the embodiment of the present invention.

Then, the endoscope bending portion 8 is further bent to pull and bring the stomach fundus 102 into contact with the part of the outer wall of the abdominal esophagus 92, from which the peritoneum 90, etc. are stripped off, as shown in FIG. 17A. Thereafter, as shown in FIG. 17B, the grasping forceps 124 are projected from the instrument channel 14 of the endoscope 2. The projecting direction of the grasping forceps 124 is adjusted by the elevator 126 provided at the opening portion of the instrument channel 14, and the grasping forceps 124 are projected from the side hole 106 of the distal end hood 105 to the outside thereof. Then, the grasping forceps 124 are pressed against tissues of the stomach fundus 102 to make the sharp edges 129 of the first and second grasping portions 128a and 128b substantially vertically puncture the tissues of the stomach fundus 102, and then the first and second grasping portions 128a and 128b are closed to grasp the tissues of the stomach fundus 102 and the tissues of the abdominal esophagus 92, with those tissues stacked together. In this state, the stacked tissues of the stomach fundus 102 and abdominal esophagus 92 are pulled into the distal end hood 105 by pulling the grasping forceps 124.

Thereafter, the needle handle 134 and the pusher handle 136 are pushed together with each other toward the sheath handle 132, and the puncture needle 116 is projected from the distal end portion of the distal end hood channel 114, and is pushed forwards. Then, the puncture needle 116 is made to puncture the tissues of the stomach fundus 102 and those of the abdominal esophagus 92. Furthermore, after being once inserted into the esophagus 82, the puncture needle 116 is made to re-puncture the tissues of the abdominal esophagus 92 and those of the stomach fundus 102.

In this state, the pusher handle 136 is pushed toward the needle handle 134 to eject the first T-bar 120a from the puncture needle 116 into the stomach 80. Then, the needle handle 134 and the pusher handle 136 are pulled together with each other in a direction away from the sheath handle 132 to pull out the puncture needle 116 from the tissues of the stomach fundus 102 and those of abdominal esophagus 92. In this state, the second T-bar 120b is ejected from the puncture needle 116 into the stomach 80.

Figure 17C:
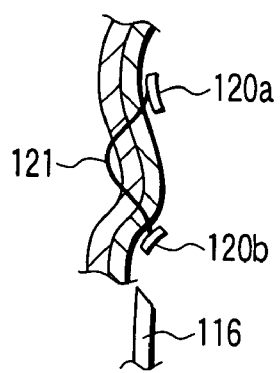
FIG. 17C is a view showing the fixed stomach fundus and the abdominal esophagus, in the treatment method according to the embodiment of the present invention.

Thereafter, the first and second grasping portions 128a and 128b are opened to release the tissues of the stomach fundus 102 and those of the abdominal esophagus 92. Then, the endoscope bending portion 8 is bent to pull out the tissues of the stomach fundus 102 and those of the abdominal esophagus 92 from the distal end hood 105. In such a manner, as shown in FIG. 17C, the stomach fundus 102 is fixed to the part of the outer wall of the abdominal esophagus 92, from which the peritoneum 90, etc. are stripped off.

Figure 18A:
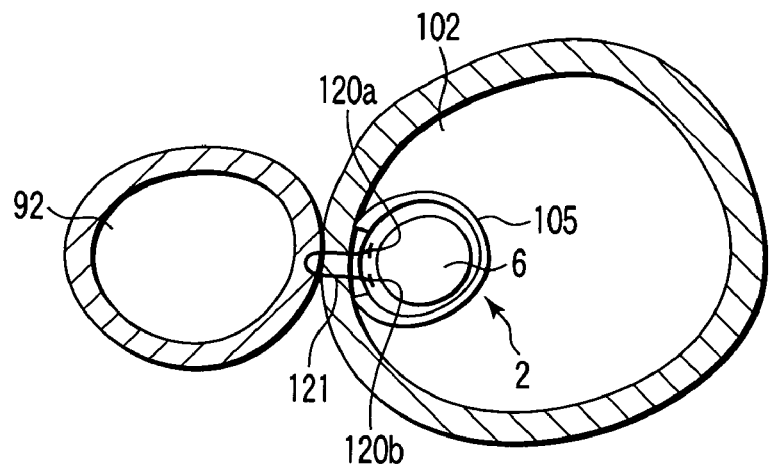
FIGS. 18A to 18C are view for use in explaining a step in which the stomach fundus is wound around the part of the outer wall of the abdominal esophagus, and is then fixed the part.
Figure 18B:
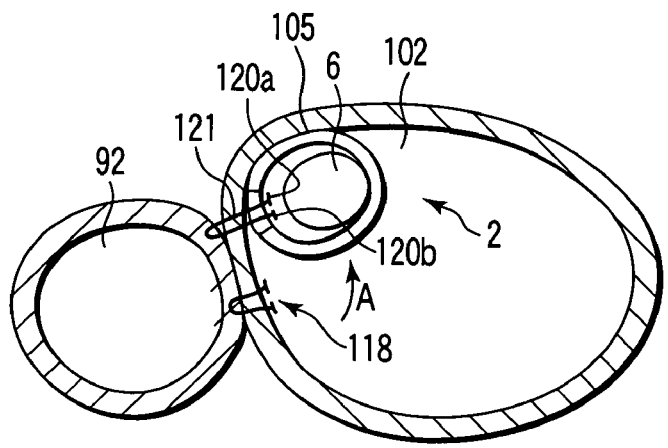
Figure 18C:
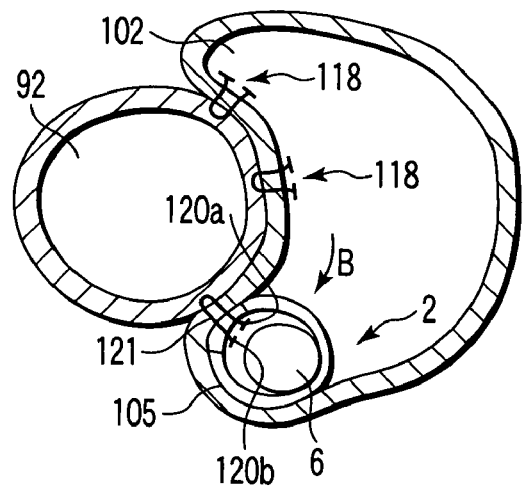

The step in which the stomach fundus 102 is wound around the abdominal esophagus 92 will be explained with reference to FIGS. 18A to 18C. As shown in FIG. 18A, first, the stomach fundus 102 is fixed to part of the abdominal esophagus 92. Then, the endoscope 2 is moved forwards and backwards to move the distal end hood 105 in the axial direction of the esophagus 82, and parts of stomach fundus 102 is fixed to corresponding parts of the esophagus 82 which are arranged apart from each other in the axial direction of the esophagus 82. The above parts of the stomach fundus 102 may be successively fixed to the parts of the abdominal esophagus 92 from the diaphragm side toward the vicinity of the gastroesophageal junction 88. Alternatively, those parts may be successively fixed from the vicinity of the gastroesophageal junction 88 toward the diaphragm side.

Subsequently, the control section 58 of the endoscope 2 is rotated to rotate the distal end portion of the endoscope 2 in the circumferential direction of the esophagus 82 as indicated by an arrow A in FIG. 18B. In this position, as mentioned above, parts of stomach fundus 102 is fixed to corresponding parts of the esophagus 82 which are arranged apart from each other in the axial direction of the esophagus 82. Furthermore, the control section 58 of the endoscope 2 is rotated in the opposite direction to rotate the distal end portion of the endoscope 2 in the opposite direction along the circumferential direction of the esophagus 82 as indicated by an arrow B in FIG. 18C. In this position also, parts of stomach fundus 102 is fixed to corresponding parts of the esophagus 82 which are arranged apart from each other in the axial direction of the esophagus 82. As a result, the stomach fundus 102 is kept to be wound around the abdominal esophagus 92.

Figure 19:
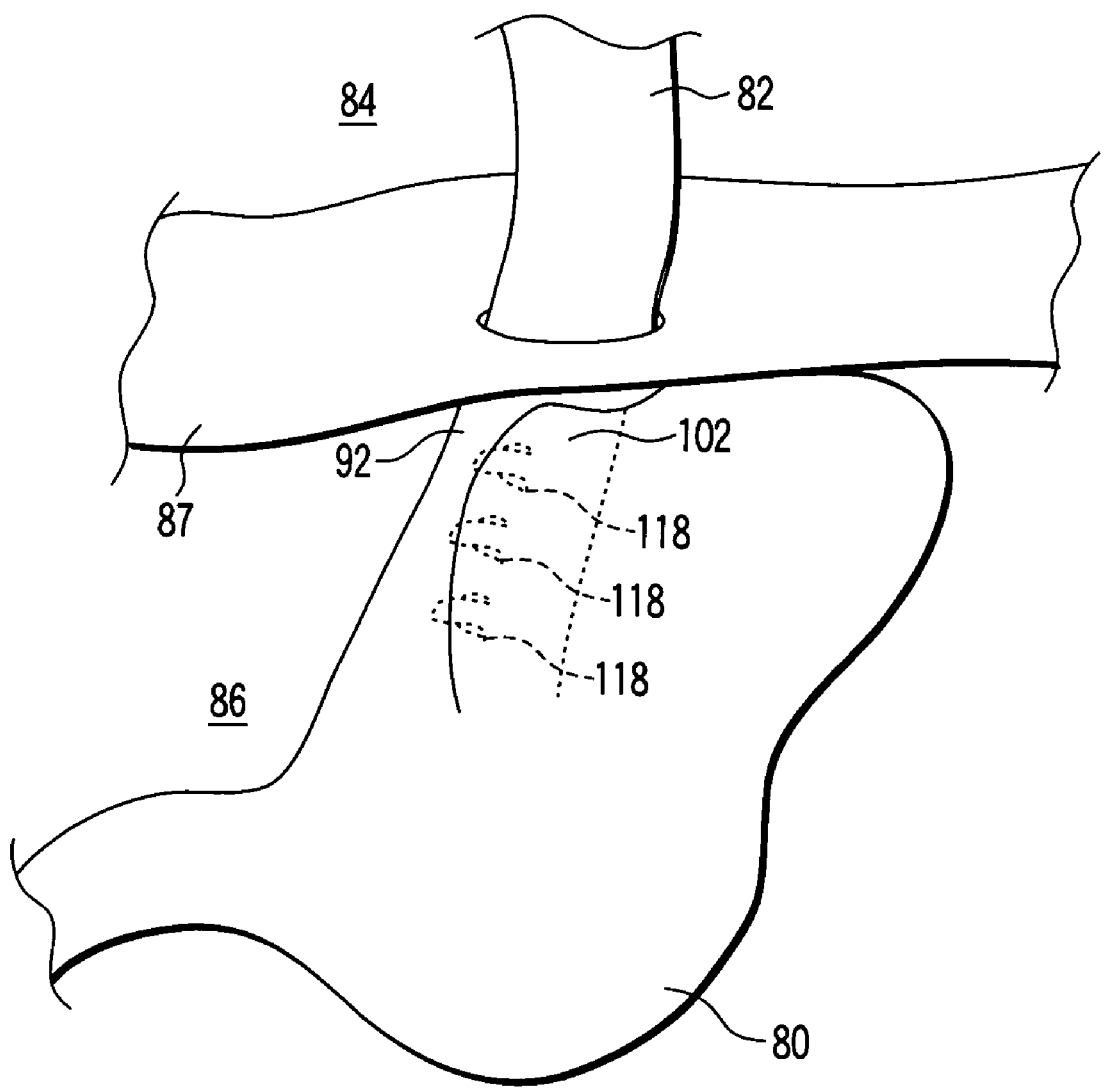
FIG. 19 is a view showing a state wherein the stomach fundus is wound around and fixed to the part of the outer wall of the abdominal esophagus, in the treatment method according to the embodiment of the present invention.

By the above step, as shown in FIG. 19, the stomach fundus 102 is wound around and fixed to the abdominal esophagus 92, from which the peritoneum, etc. are stripped off.

In the embodiment, part of the peritoneum 90, etc. covering the abdominal esophagus 92 is perorally removed. Then, the stomach fundus 102 is perorally pulled to the part of the abdominal esophagus 92, from which the peritoneum 90, etc. are removed. Then, the pulled stomach fundus 102 is perorally fixed to the part of the abdominal esophagus 92, from which the peritoneum 90, etc. are removed. That is, in the treatment method according to the embodiment, all the steps are perorally carried out. Thus, in the treatment method, the invasiveness is low, and the burden on a patient is small.

Furthermore, when the stomach fundus 102 wound around the abdominal esophagus 92 expands, the abdominal esophagus 92 is squashed and closed. It should be noted that the stomach fundus 102 expands and contracts to a sufficiently great degree, as compared with expanding and contacting of other portions of the stomach 80, e.g., the gastroesophageal junction 88 and the vicinity thereof. Thus, when the treatment method according to the present invention is applied, the abdominal esophagus 92 is sufficiently squashed, compared with the case where other portions of the stomach 80, e.g., the gastroesophageal junction 88 and the vicinity thereof, are fixed to the abdominal esophagus 92, as a result of which reflux is effectively prevented.

From the anatomical point of view, the peritoneum 90 extends in such a way as to cover the abdominal esophagus 92 from the diaphragm 87 to the gastroesophageal junction 88, and the abdominal esophagus 92 barely exposes to the inside of the peritoneal cavity 86. Thus, in the case where the peritoneum 90 is not removed from the abdominal esophagus 92, even if the stomach fundus 102 is pulled to the abdominal esophagus 92, the outer wall of the stomach fundus 102 and that of the abdominal esophagus 92 cannot be directly fixed to each other. This is because the peritoneum 90 is present between the stomach fundus 102 and the abdominal esophagus 92. Then, if the stomach fundus 102 is fixed to the peritoneum 90 between the abdominal esophagus 92 and the stomach fundus 102, expanding and contracting of the stomach fundus 102 is absorbed by those of the peritoneum 90, which is membranous and can expand and contract independent of other tissues. Thus, the expanding and contracting of the stomach fundus 102 are not transmitted to the abdominal esophagus 92. Accordingly, it cannot be expected that it squashes the abdominal esophagus 92.

In the embodiment, part of the peritoneum 90, etc. of the abdominal esophagus 92 are removed through the peritoneal cavity, and the stomach fundus 102 is fixed to part of the abdominal esophagus 92, from which the peritoneum 90, etc. are removed. Thus, expanding and contacting of the stomach fundus 102 are not absorbed by the peritoneum 90, and the abdominal esophagus 92 is sufficiently squashed, as compared with the case where the stomach fundus 102 is fixed to the peritoneum 90. Accordingly, the reflux is effectively prevented.

Moreover, the bending portion 46 which is operated to be bent is provided at the bending-overtube 40 into which the endoscope 2 is to be inserted. Therefore, the peritoneum 90, etc. can be stripped off by the following operation: the bending-overtube 40 is moved from the stomach 80 into the peritoneal cavity 86 through the opening portion 100 formed in the stomach 80; the bending portion 46 is bent such that the distal end portion of the bending-overtube 40 faces the abdominal esophagus 92; the endoscope 2 is pushed forwards within the bending-overtube 40; and the distal end portion of the endoscope 2 is moved toward the abdominal esophagus 92. That is, stripping off of the peritoneum 90, which cannot be achieved simply by inserting the endoscope 2 into the peritoneal cavity 86 easily, can be appropriately performed by using the bending-overtube 40 including the bending portion 46.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment method comprising:
    perorally inserting an apparatus into a stomach;
    introducing a distal end portion of the apparatus inserted in the stomach from the stomach into a peritoneal cavity;
    removing a membrane of part of an outer wall of an abdominal esophagus;
    returning the distal end portion of the apparatus introduced in the peritoneal cavity into the stomach;
    perorally pulling a stomach fundus to the part of the outer wall of the abdominal esophagus; and
    perorally fixing the pulled stomach fundus to the part of the outer wall of the abdominal esophagus.

2. The treatment method according to claim 1, wherein the introducing the distal end portion of the apparatus includes:
    incising part of the stomach; and
    moving the apparatus from the stomach into the peritoneal cavity through the incised part.

3. The treatment method according to claim 2, wherein the incising the part of the stomach includes incising the part of the stomach by using an instrument projected from an instrument channel of an endoscope provided in the apparatus.

4. The treatment method according to claim 3, wherein the moving the apparatus into the peritoneal cavity includes:
    moving the endoscope provided in the apparatus from the stomach into the peritoneal cavity through the incised part; and
    moving a tubular member, in which the endoscope is inserted, from the stomach into the peritoneal cavity along the endoscope through the incised part.

5. The treatment method according to claim 2, wherein the returning the distal end portion of the apparatus introduced in the peritoneal cavity into the stomach includes:
    returning the distal end portion of the apparatus from the peritoneal cavity into the stomach through the incised part; and
    closing the incised part.

6. The treatment method according to claim 1, wherein the removing the membrane of the part of the outer wall of the abdominal esophagus includes:
    bringing the distal end portion of the apparatus which is introduced in the peritoneal cavity, close to the outer wall of the abdominal esophagus; and
    stripping off the membrane of the part of the outer wall of the abdominal esophagus.

7. The treatment method according to claim 6, wherein the bringing the distal end portion of the apparatus close to the outer wall of the abdominal esophagus includes:
    introducing a tubular member provided in the apparatus into the peritoneal cavity;
    bending the tubular member introduced in the peritoneal cavity to make a distal end opening portion of the tubular member face the abdominal esophagus; and projecting an endoscope inserted in the tubular member, from the distal end opening portion of the tubular member, and moving the endoscope forwards.

8. The treatment method according to claim 6, wherein the stripping off the membrane of the part of the outer wall of the abdominal esophagus includes incising and ablating the membrane of the part of the outer wall of the abdominal esophagus by using an instrument projected from an instrument channel of an endoscope provided in the apparatus.

9. The treatment method according to claim 8, wherein the incising and ablating the membrane of the part of the outer wall of the abdominal esophagus includes:
   grasping the membrane of the part of the outer wall of the abdominal esophagus by using a first instrument projected from a first channel of the endoscope;
   pulling the gasped membrane by using the first instrument; and
   incising and ablating the pulled membrane by using a second instrument projected from a second instrument channel of the endoscope.

10. The treatment method according to claim 1, wherein the pulling the stomach fundus to the part of the outer wall of the abdominal esophagus includes:
   abutting the distal end portion of the apparatus inserted in the stomach against an inner surface of the stomach fundus; and
   moving the distal end portion of the apparatus which is abutted against the inner surface of the stomach fundus, towards the part of the outer wall of the abdominal esophagus.

11. The treatment method according to claim 10, wherein the abutting the distal end portion of the apparatus inserted in the stomach against the inner surface of the stomach fundus includes abutting an abut member provided at a distal end portion of an endoscope provided in the apparatus against the inner surface of the stomach fundus.

12. The treatment method according to claim 10, wherein the moving the distal end portion of the apparatus towards the part of the outer wall of the abdominal esophagus includes bending a bending portion of an endoscope provided in the apparatus.

13. The treatment method according to claim 1, wherein the fixing the pulled stomach fundus to the part of the outer wall of the abdominal esophagus includes:
   pulling tissues of the stomach fundus and tissues of the abdominal esophagus into a tube member provided at a distal end portion of an endoscope provided in the apparatus through a communication portion formed in the tube member; and
   fixing the tissues of the stomach fundus and the tissues of the abdominal esophagus which are pulled into the tube member to each other.

14. The treatment method according to claim 13, wherein the fixing the tissues of the stomach fundus and the tissues of the abdominal esophagus to each other includes:
   making a hollow puncture in both the tissues of the stomach fundus and the tissues of the abdominal esophagus using a hollow puncture needle;
   ejecting a first engagement portion of a placement member contained in the hollow puncture needle, and engaging the first engagement portion with the tissue of the stomach fundus;
   pulling out the hollow puncture needle from both the tissues of the stomach fundus and the tissues of the abdominal esophagus; and
   ejecting a second engagement portion of the placement member from the hollow puncture needle, and engaging the second engagement portion with the tissue of the stomach fundus.

* * * * *